US006647778B2

(12) United States Patent
Sparks

(10) Patent No.: US 6,647,778 B2
(45) Date of Patent: Nov. 18, 2003

(54) INTEGRATED MICROTUBE SENSING DEVICE

(75) Inventor: Douglas Ray Sparks, Whitemore Lake, MI (US)

(73) Assignee: Integrated Sensing Systems, Ypsilanti, MI (US)

(*) Notice: Subject to any disclaimer, the term of this patent is extended or adjusted under 35 U.S.C. 154(b) by 0 days.

(21) Appl. No.: 10/064,190

(22) Filed: Jun. 20, 2002

(65) Prior Publication Data

US 2002/0194908 A1 Dec. 26, 2002

Related U.S. Application Data

(60) Provisional application No. 60/299,348, filed on Jun. 20, 2001, and provisional application No. 60/327,833, filed on Oct. 9, 2001.

(51) Int. Cl.$^7$ ................................................ G01F 1/68
(52) U.S. Cl. ................................................ 73/204.26
(58) Field of Search ...................... 73/204.26, 861.357, 73/861.355, 861.356

(56) References Cited

U.S. PATENT DOCUMENTS

| 4,729,243 A | * | 3/1988 | Friedland et al. ....... 73/861.355 |
| 5,663,509 A | * | 9/1997 | Lew et al. ............. 73/861.357 |
| 5,700,958 A | * | 12/1997 | Lew et al. ............. 73/861.357 |
| 6,164,140 A | * | 12/2000 | Kalinoski ............. 73/861.357 |
| 6,286,373 B1 | * | 9/2001 | Lister et al. ........... 73/861.355 |
| 6,477,901 B1 | * | 11/2002 | Tadigadapa et al. ..... 73/861.352 |

* cited by examiner

Primary Examiner—Edward Lefkowitz
Assistant Examiner—Jewel V. Thompson
(74) Attorney, Agent, or Firm—Gary M. Hartman; Domenica N.S. Hartman; Hartman and Hartman

(57) ABSTRACT

A sensing device that comprises a micromachined tube on a substrate for resonant sensing of mass flow and density of a fluid flowing through the tube. The sensing device further incorporates on the same substrate at least a second micromachined tube configured for sensing another property of the fluid, such as pressure, viscosity and/or temperature.

32 Claims, 4 Drawing Sheets

INTEGRATED MICROTUBE SENSING DEVICE

CROSS REFERENCE TO RELATED APPLICATIONS

This application claims the benefit of U.S. Provisional Application No. 60/299,348, filed Jun. 20, 2001, and U.S. Provisional Application No. 60/327,833, filed Oct. 9, 2001.

BACKGROUND OF INVENTION

1. Field of the Invention

The present invention generally relates to micromachined sensing devices and methods. More particularly, this invention relates to devices and methods that integrate multiple sensing techniques and elements on a single substrate.

2. Description of the Related Art

A process and design for fabricating resonant mass flow and density sensors using a silicon micromachining technique are disclosed in commonly-assigned U.S. Pat. No. 6,477,901 to Tadigadapa et al. As used herein, micromachining is a technique for forming very small elements by bulk etching a substrate (e.g., a silicon wafer), or by surface thin-film etching, the latter of which generally involves depositing a thin film (e.g., polysilicon or metal) on a sacrificial layer (e.g., oxide layer) on a substrate surface and then selectively removing portions of the sacrificial layer to free the deposited thin film. In the process disclosed by Tadigadapa et al., wafer bonding and silicon etching techniques are used to produce a suspended silicon tube on a wafer. The tube is vibrated at resonance, by which the flow rate and density of a fluid flowing through the tube can be determined.

While well suited for the function of sensing flow rates and densities of fluids, it would be advantageous if other properties of a fluid could be determined on the same wafer, yielding an integrated device that is more flexible in meeting system needs.

SUMMARY OF INVENTION

The present invention provides a sensing device that comprises a micromachined tube on a substrate, such as of the type disclosed in U.S. Pat. No. 6,477,901 to Tadigadapa et al. for resonant sensing of mass flow and density of a fluid flowing through the tube. The sensing device of this invention further incorporates on the same substrate at least a second micromachined tube configured for sensing another property of the fluid, such as pressure, viscosity and/or temperature.

The sensing device of this invention comprises a first tube micromachined on a substrate and comprising a fluid inlet, a fluid outlet, and a freestanding portion between the fluid inlet and the fluid outlet so as to define a continuous passage for a fluid flowing through the first tube. The freestanding portion is spaced apart from a first surface of the substrate, and means is provided for vibrating the freestanding portion at a resonant frequency thereof. In addition, means is provided for sensing movement of the freestanding portion of the first tube. A second micromachined tube is fabricated on the substrate. According to a first embodiment of the invention, the second tube is in series with the first tube such that the fluid flows through both the first and second tubes. The second tube may have a bridge portion spaced apart from a second surface of the substrate, and that is operable to deflect toward and away from the second surface in response to a change in pressure of the fluid flowing through the second tube, such that sensing the proximity of the bridge portion to the second surface of the substrate is indicative of the pressure of the fluid flowing through the first and second tubes.

According to a second embodiment of the invention, the sensing device may further comprise a third micromachined tube on the substrate and in series with the first and second tubes, such that the fluid flows through the second, first and third micromachined tubes, respectively. Similar to the second tube, the third tube may have a bridge portion spaced apart from the substrate and operable to deflect toward and away from the substrate in response to a change in pressure of the fluid flowing through the third tube. By also sensing the proximity of the bridge portion of the third tube to the substrate, the viscosity of the fluid can be determined based on the relative pressures sensed with the second and third tubes.

According to third and fourth embodiments of the invention, the second tube comprises a cantilevered portion spaced apart from a second surface of the substrate member. In the third embodiment, the cantilevered portion is operable to sense motion of the sensing device, while in the fourth embodiment of the invention the cantilevered portion thermally communicates with the first tube for sensing the temperature of the fluid flowing through the first tube. In this embodiment, the cantilevered portion is vibrated at a resonant frequency thereof, and changes in temperature of the fluid flowing through the first tube is sensed by detecting changes in the resonant frequency of the cantilevered portion.

Various additional features can be incorporated into the sensing device of the present invention. For example, the device may be equipped with a cap hermetically bonded to the substrate so as to define a hermetically-sealed evacuated enclosure containing the first and second tubes. If the second tube is operable as a temperature sensor, the cap can be adapted to shield the second tube from thermal radiation, or shield all but certain wavelengths of interest, e.g., infrared (IR). As another example, one or more metal layers can also be incorporated into the sensing device, such as for sensing the temperature of the fluid by sensing changes in electrical resistance of a metal layer, or for sensing the electrical conductivity, dielectric constant and pH of the fluid with two metal layers spaced apart and in contact with the fluid. Yet another feature that can be integrated with the sensing device is one or more stress-sensing members configured to be substantially similar to the first and/or second tubes but through which the fluid does not flow, so that movement of the stress-sensing member caused by extraneous sources can be sensed and used to compensate the output obtained from the first and/or second tubes. Finally, the sensing device can be provided with electrodes contacting portions of the first tube at or near the fluid inlet and the fluid outlet thereof, and means for flowing a current between the electrodes and through the first tube so as to heat and maintain the fluid flowing therethrough at a desired temperature. In this manner, more accurate density, viscosity and/or flow measurements of the fluid can be obtained.

In view of the above, it can be seen that the present invention provides for the integration and design of various sensing techniques in a resonant micromachined tube and process. Such devices include pressure, temperature, viscosity, and optical/IR sensors, which make possible a variety of improved chemical or biochemical sensors and motion sensors. Further improvements are achieved by integrated stress compensation into the micromachining process and design. By incorporating on the same wafer multiple structures capable of sensing multiple properties of a fluid, the present invention is able to provide an integrated device that is more capable of meeting various requirements of a fluid analysis system.

Other objects and advantages of this invention will be better appreciated from the following detailed description.

DETAILED DESCRIPTION

Figure 1:
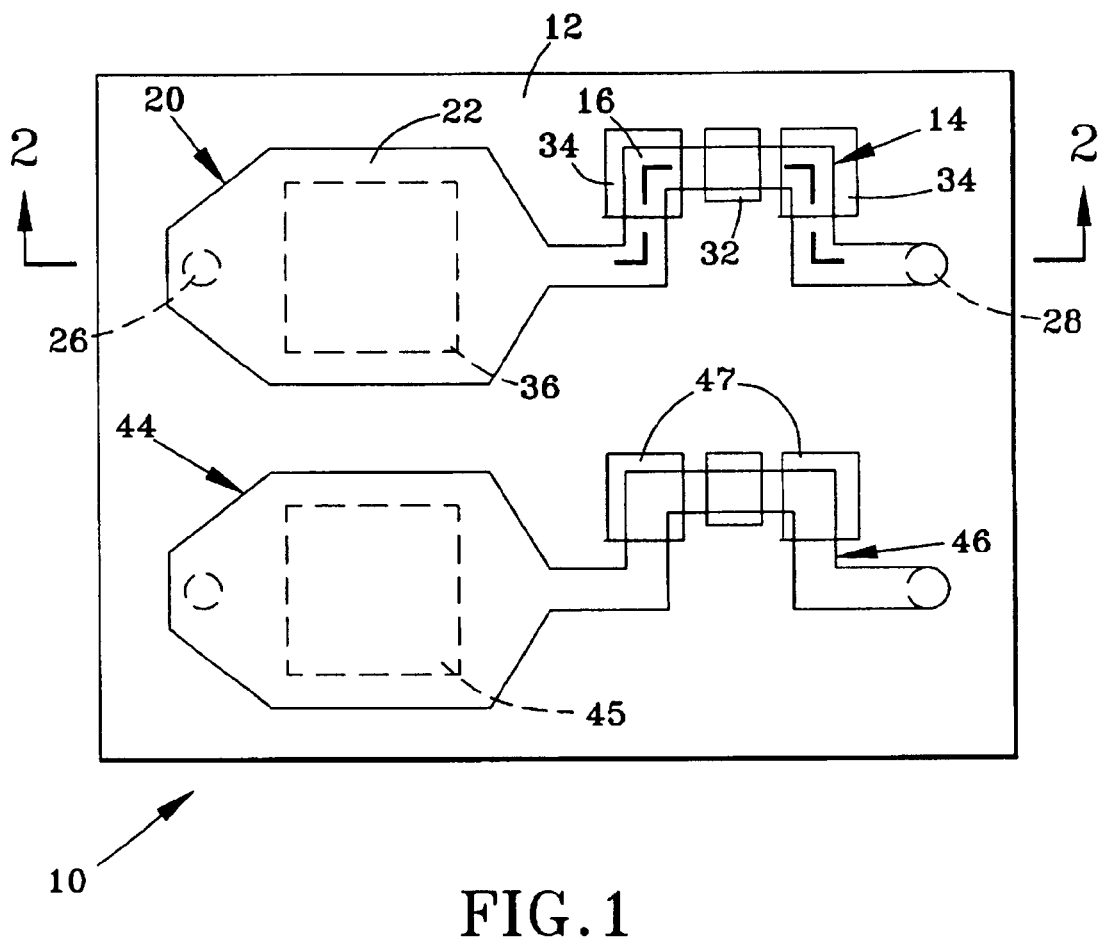
FIGS. 1 and 2 are plan and cross-sectional views, respectively, of a sensing device with two micromachined tubes in fluidic series in accordance with a first embodiment of this invention.
Figure 2:
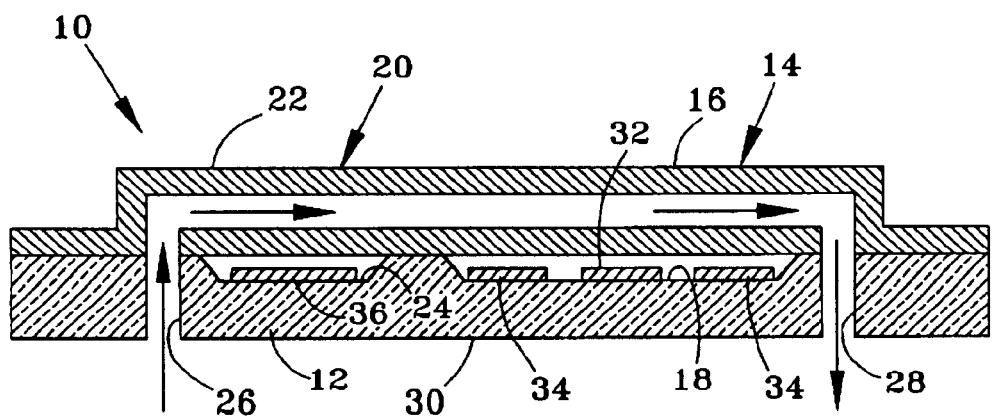

FIGS. 1 and 2 represent a sensing device 10 in accordance with a first embodiment of the present invention. The device 10 is represented as being fabricated on a substrate 12, which can be formed of silicon or another semiconductor material, quartz, ceramic, metal or a composite material. A first tube 14 is supported by the substrate 12 so as to have a freestanding portion 16 suspended above a first surface 18 of the substrate 12. A second tube 20 is also represented as being supported by the substrate 12, with a bridge portion 22 of the tube 20 being spaced above a second surface 24 of the substrate 12. According to the invention, each of the tubes 14 and 20 is micromachined from silicon or another semiconductor material, quartz, ceramic, metal or composite material. The tubes 14 and 20 can either be fabricated entirely from layers of the chosen materials deposited on the substrate 12, or fabricated in part by etching the substrate 12, as will be discussed in more detail below.

The tube 14 is shown in FIGS. 1 and 2 as being adapted to serve as a conduit through which a fluid flows while the tube 14 is vibrated for the purpose of ascertaining certain properties of the fluid, preferably using Coriolis force principles in accordance with U.S. Pat. No. 6,477,901 to Tadigadapa et al., incorporated herein by reference. For this purpose, the freestanding portion 16 of the tube 14 is generally U-shaped, though other shapes—both simpler and more complex—are within the scope of this invention, and the freestanding portion 16 is vibrated in a direction perpendicular to the surface 18 of the substrate 12 (into the plane of FIG. 1), preferably at or near its resonant frequency. Fluid enters the device 10 through a fluid inlet 26 and exits the tube 14 through a fluid outlet 28, both of which are represented in FIG. 2 as being etched or otherwise formed in a surface 30 of the substrate 12 opposite the tube 14. During half of the vibration cycle in which the tube 14 moves upward, the freestanding portion 16 has upward momentum as the fluid travels around the tube bends, and the fluid flowing out of the freestanding portion 16 resists having its vertical motion decreased by pushing up on that part of the freestanding portion 16 nearest the fluid outlet 28. The resulting force causes the freestanding portion 16 of the tube 14 to twist. As the tube 14 moves downward during the second half of its vibration cycle, the freestanding portion 16 twists in the opposite direction. This twisting characteristic is referred to as the Coriolis effect, and the degree to which the freestanding portion 16 of the tube 14 deflects during a vibration cycle as a result of the Coriolis effect can be correlated to the mass flow rate of the fluid flowing through the tube 14, while the density of the fluid is proportional to the frequency of vibration.

The shape and size of the tube 14 are chosen to provide an adequate flow capacity for the fluid and to have suitable vibration parameters for the intended fluid(s) to be evaluated with the device 10. Because micromachining technologies are employed to fabricate the tube 14, the size of the tube 14 can be extremely small, such as lengths of about 0.5 mm and cross-sectional areas of about 250 $\mu$m$^2$, with smaller and larger tubes also being within the scope of this invention. Because of the ability to produce the tube 14 at such miniaturized sizes, the device 10 can be used to process very small quantities of fluid for analysis.

The tube 14 is preferably driven at resonance, with the resonant frequency of the tube 14 being controlled by its mechanical design (shape, size, construction and materials). Resonant frequencies will generally be in the range of about 1 kHz to 1100 kHz. The amplitude of vibration is preferably adjusted through the means used to vibrate the tube 14. As shown in FIGS. 1 and 2, a drive electrode 32 is located beneath the tube 14 on the surface 18 of the substrate 12. In this embodiment, the tube 14 is formed of doped silicon and can therefore serve as an electrode that can be capacitively coupled to the drive electrode 32, enabling the electrode 32 to capacitively (electrostatically) drive the tube 14. However, it is foreseeable that the tube 14 could be formed of a nonconductive material, and a separate electrode formed on the tube 14 opposite the electrode 32 for vibrating the tube 14 electrostatically. An alternative driving technique is to provide a piezoelectric element on an upper surface of the tube 14 to generate alternating forces in the plane of the tube 14 that flex the freestanding portion 16 of the tube 14 in directions normal to the plane of the tube 14. Other alternatives are to drive the freestanding portion 16 of the tube 14 magnetically, thermally, or by another actuation technique. Also shown in FIGS. 1 and 2 are sensing electrodes 34 for providing feedback to the drive electrode 32 to enable the vibration frequency to be controlled with appropriate circuitry (not shown) while also sensing the deflection of the tube 14 relative to the substrate 12. The sensing electrodes 34 can sense the tube 14 capacitively or in any other suitable manner capable of sensing the proximity or motion of the tube 14.

In contrast to the first tube 14, the second tube 20 on the substrate 12 is adapted for sensing the pressure of the fluid flowing through the device 10, and therefore is not required to vibrate. As shown in FIGS. 1 and 2, fluid flows from the fluid inlet 26 through the second tube 20 before entering the first tube 14. The shape and size of the tube 20 are chosen to promote flexure of the lower wall of the tube 20 in response to changes in fluid pressure. Again, micromachining technologies permit the bridge portion 22 of the second tube 20 to be accurately fabricated to extremely small dimensions, such as a length of about one millimeter and a transverse width (parallel to the plane of the substrate 12) of about one millimeter. Preferred widths for the tube 20 are greater than that for the tube 14 in view of their different functions. Similar to the first tube 14 and its sensing electrodes 34, movement of the second tube 20 relative to the underlying surface 24 of the substrate 12 can be sensed by forming the tube 20 of doped silicon, enabling the bridge portion 22 of the tube 20 to serve as an electrode that can be capacitively coupled to a sensing electrode 36 on the substrate surface 24. Alternatively, the bridge portion 22 of the tube 20 can be sensed piezoelectrically, magnetically, or by another suitable technique.

Figure 3:
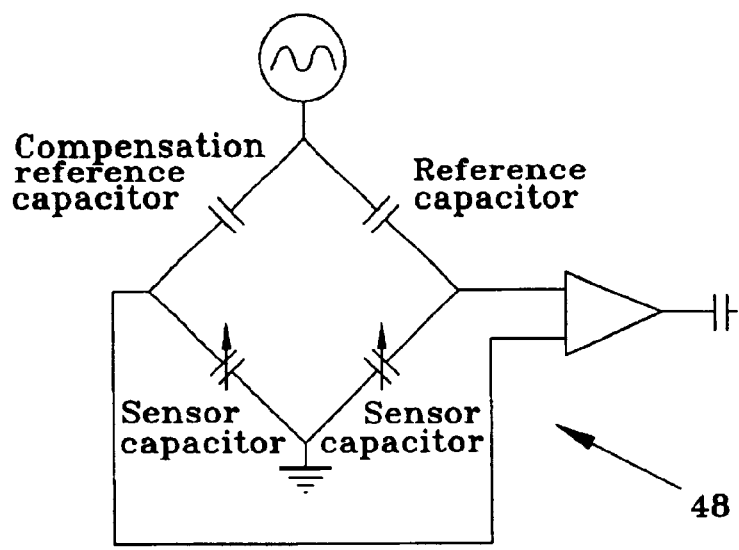
FIG. 3 is a schematic of a circuit for compensating for stress and packaging-related distortions of the micromachined tubes of FIG. 1.

FIG. 1 also depicts a technique for addressing the problem of packaging and thermal stresses that can be encountered with micromachined sensor packages. Rigid package mounting typically employed for micromachined devices, including that of FIGS. 1 and 2, can result in the generation of high stress fields that can shift device performance. In FIG. 1, packaging stresses are compensated for by sensing the deflection or movement of a second pair of tubes 46 and 44 configured to be essentially identical to the tubes 14 and 20, respectively. However, fluid is not flowed through the tubes 44 and 46, so that deflection and other movement of the tubes 44 and 46 is associated primarily with packaging-related stresses. When packaging-related stresses cause the freestanding and bridge portions 16 and 22 of the tubes 14 and 20, respectively, to warp or shift, the corresponding output from the sensing electrodes 34 and 36 of the freestanding and bridge portions 16 and 22 can be nulled out by sensing a similar shift in the tubes 44 and 46 with appropriate sensors 45 and 47, which function as compensating capacitive structures mounted on the same substrate 12. All four elements can form part of a capacitive bridge or differential amplifier element, such as the bridge 48 schematically illustrated in FIG. 3. While FIG. 1 shows the compensating tubes 44 and 46 as being essentially identical to the tubes 14 and 20, the tubes 44 and 46 could by smaller than the tubes 14 and 20. Furthermore, it is foreseeable that simple straight cantilevers could be employed as compensation elements. A complete four element capacitive bridge can be fashioned on the substrate 12 in this manner with any combination of sensing tubes 14 and 20 and compensation features. Additional circuitry to buffer and amplify the signal can also be provided on the substrate 12.

Figure 4:
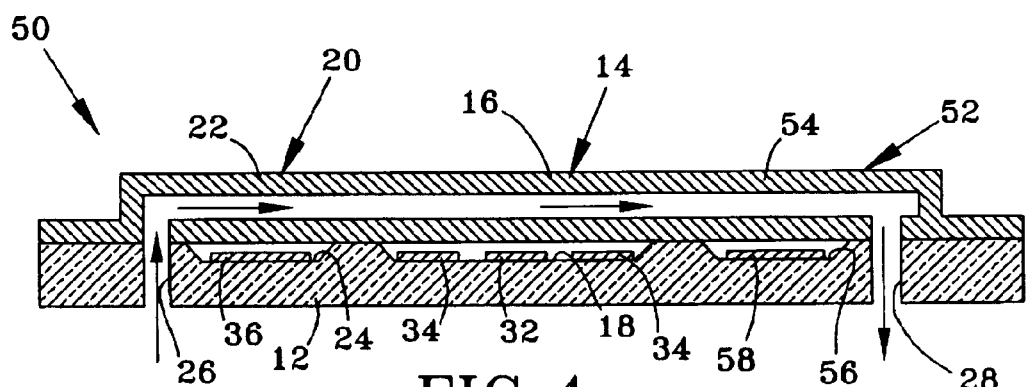
FIG. 4 is a cross-sectional view of a sensing device with three micromachined tubes in accordance with a second embodiment of this invention.

In FIG. 4, fluid viscosity is determined by a sensing device 50 modified to have a pressure-sensing third tube 52. Elements in FIG. 4 similar to elements of FIGS. 1 and 2 are identified with the same corresponding reference numbers. For example, the sensing device 50 is equipped with a resonant tube 14 and a pressure-sensing tube 20 upstream of the tube 14. In FIG. 4, the third tube 52 is similar in construction and function as the second tube 20, i.e., defines a bridge portion 54 responsive to changes in pressure, and whose movement is sensed by an electrode 58 located on a surface 56 of the substrate 12 over which the bridge portion 54 is suspended. As such, two pressure sensors are integrated with the flow and density-sensing capability provided by the first tube 14. The third tube 52 is located adjacent the fluid outlet 28, so that the device 10 is equipped with pressure sensors near the fluid inlet and outlet 26 and 28. The pressure drop measured as occurring between inlet and outlet 26 and 28 can be correlated to the viscosity of the fluid flowing through the tube 14.

Figure 5:
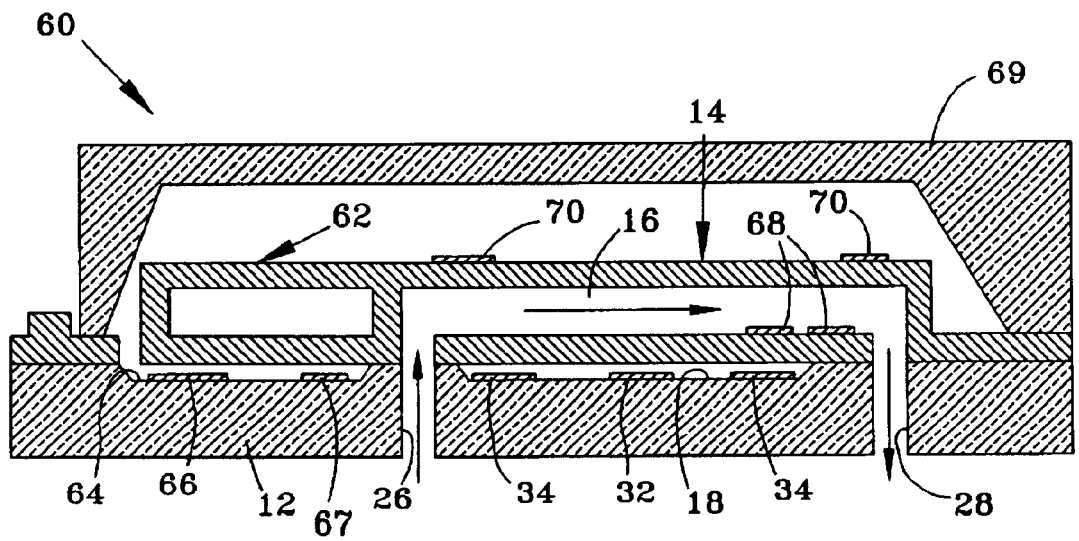
FIG. 5 is a cross-sectional view of a sensing device with two micromachined tubes, one of which is cantilevered, in accordance with third and fourth embodiments of this invention.

FIG. 5 represents a sensing device 60 in accordance with third and fourth embodiments of the invention, again shown as being equipped with similar elements identified with the same corresponding reference numbers as those in FIGS. 1 and 2. The sensing device 60 in FIG. 5 differs by fabricating a micromachined tube 62 to have a cantilevered portion extending out over a the surface 64 of the substrate 12. According to the third embodiment, the cantilevered tube 62 is used to measure the temperature of the fluid flowing through the resonating tube 14. It is known that the Young's and shear modulus of materials change with temperature. For silicon resonators this change causes the resonant frequency to shift with temperature, which can then be sensed with an appropriate sensing element. The tube 62 can be fabricated in the same manner as the resonant tube 14, but without the requirement for fluid flow such that the tube 62 is not required to form a fluid circuit. The tube 62 is shown as being formed immediately adjacent the tube 14, so that any temperature change in the fluid will be transmitted to the tube 62 by thermal conduction. As shown in FIG. 5, a sensing electrode 66 and a drive electrode 67 are located on the surface 64 of the substrate 12 beneath the cantilevered tube 62. As with previous embodiments, the tube 62 is preferably formed of doped silicon and can therefore serve as an electrode that can be capacitively coupled to the sensing and drive electrodes 66 and 67, though it is foreseeable that the tube 62 could be formed of a nonconductive material and equipped with a separate electrode.

As also shown in FIG. 5, the sensing device 60 can be enclosed by a silicon or glass cap 69 to reduce external sources of temperature change such as radiation, convection and conduction from the surrounding environment. The resonant tubes 14 and 62 of this invention also benefit from vacuum packaging to increase their output signals. A variety of package and wafer methods exist to vacuum package devices. These include solder or weld hermetic packages, and wafer bonding using glass frit, solder, eutectic alloy and anodic bonding. Since metal runners are used to transmit the electrical signals, and the capacitive signals produced by the tubes 14, 20, 52 and 62 are relatively small, wafer to wafer bonding methods are preferred. Therefore, in the preferred embodiment of this invention, the bond between the cap 69 and the substrate 12 is hermetic, and the enclosure formed by the substrate 12 and cap 69 is evacuated to enable the tubes 14 and 62 to be driven efficiently at high Q values without damping. A preferred material for the cap 69 is silicon, allowing silicon-to-silicon bonding techniques to be used. The choice of material for the cap 69 may depend on whether it is desired to completely block incident radiation or to filter certain ranges of wavelengths by applying one or more coatings to the cap 69. By changing the optical properties of the cap 69, the sensing device 60 can be rendered sensitive to certain wavelengths, such as infrared (IR), that may be useful for chemical and biochemical analysis.

According to the fourth embodiment of the invention, the cantilevered tube 62 shown in FIG. 5 can be used to sense motion, which can be of use in a fluidic application for the purpose of monitoring pipe vibration and shock. For this embodiment, the cantilevered tube 62 can be operated capacitively and/or at resonance with the sensing and drive electrodes 66 and 67. The bridge portions 22 of the tube 20 could also be used to sense motion in a manner similar to the cantilevered tube 62.

An alternative temperature sensor can be provided in any of the sensing devices 10, 50 and 60 using one or more metal layers of the type employed to form the electrodes 32, 34, 36, 66 and 67, and their associated conductive runners. For example, a resistivetemperature sensor can be formed by a thin-film metal layer of platinum, palladium or nickel, in accordance with known practices. FIG. 5 shows a pair of electrodes 70 formed on the exterior of the tube 14, one or both of which can be used as a resistive-based temperature sensor. Alternatively, by applying an electrical potential across the electrodes 70, a current can be passed through the tube 14 to raise and maintain the temperature of the tube 14 and the fluid flowing therethrough by Joule heating. Precise temperature control is required for accurate density, viscosity and flow measurements taken with the tubes 14 and 20 of FIGS. 1 through 4. The electrodes 70 make relatively rapid temperature changes and control possible within the environment of the device 60, in which other external heat sources cannot rapidly alter the temperature of the tube 14 because the tube 14 is bonded to poor conductors (e.g., glass) and suspended in a vacuum, which prevents convective heating or cooling of the tube. A control circuit (not shown) can be used to adjust and maintain the desired temperature using either the resonant frequency of the tube 14, the resonant cantilevered tube 62, or a thin-film metal resistor of a type described above as a temperature sensor.

Metal layers suitable for use as a resistive-based temperature sensor can also be employed to form an integrated fluidic sensor capable of measuring the electrical conductivity, dielectric constant and/or pH of the fluid flowing through any one of the devices 10, 50 and 60. In FIG. 5, this aspect of the invention is represented by two closely-separated metal electrodes 68 located within the passage formed by the resonator tube 14, though the electrodes 68 could be placed elsewhere in the devices or on a package header to which the devices might be attached. Electrical conductivity of the fluid sensed by measuring DC resistance as the fluid flows over the two electrodes 68. By applying an AC bias to the electrodes 68, the dielectric constant of the fluid can be measured. Both of these properties can be useful to identify additives and impurities in a fluid. Coupling this capability to determine these properties in combination with density and viscosity measurements obtained with the resonator tube 14 can greatly improve the ability to distinguish subtle differences between fluid samples. Finally, if iridium is used as the metal for the electrodes 68, oxidation to form an $IrO_2$ electrode can be used to produce an integrated pH sensor in accordance with known techniques in the art.

From the Figures, it can be seen that the tubes 20, 52 and 62 and other sensing elements of this invention can be fabricated with the same silicon, metal and glass layers used to form the resonant tube 14. A particularly suitable process for fabricating the tubes 14, 20, 52 and 62 is disclosed in U.S. Pat. No. 6,477,901 to Tadigadapa et al., which is incorporated herein by reference. The etching and corrosion resistance of the fluid-carrying tubes 14, 20 and 52 can be improved by forming their inner surfaces to be heavily doped with a dopant, such as boron, aluminum or gallium. The presence of a doped layer also allows for the use of a wider range of chemicals and durations used in the fabrication of the tubes 14, 20, 52 and 62. FIGS. 6 through 12 represent such a process, in which a silicon wafer is etched to form a trench for each suspended feature required for the device 10, 50 or 60, i.e., the resonant tube 14, the pressure-sensing tubes 20 and 52, and the cantilevered tube 62. The fabrication of the trench for the tube 20 is represented in FIGS. 6 through 12 for simplicity.

Figure 6:
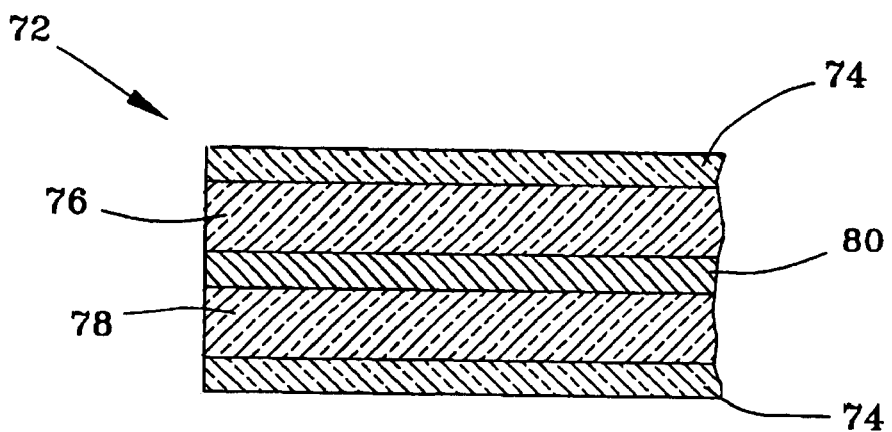
FIGS. 6 through 12 represent a sequence of processing steps for producing the sensing devices of FIGS. 1 through 5.
Figure 7:
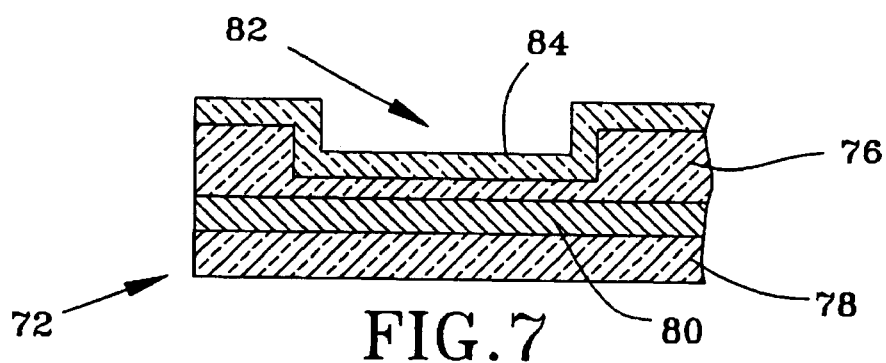
Figure 8:
Figure 9:
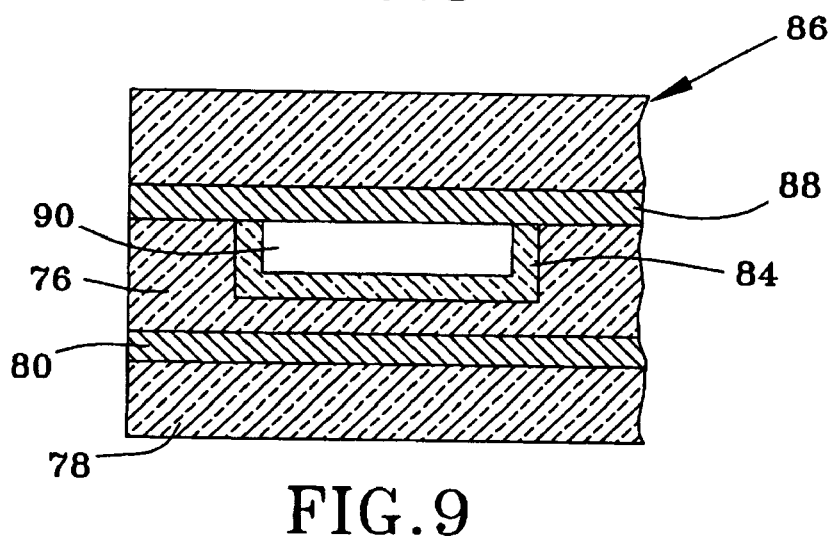
Figure 10:
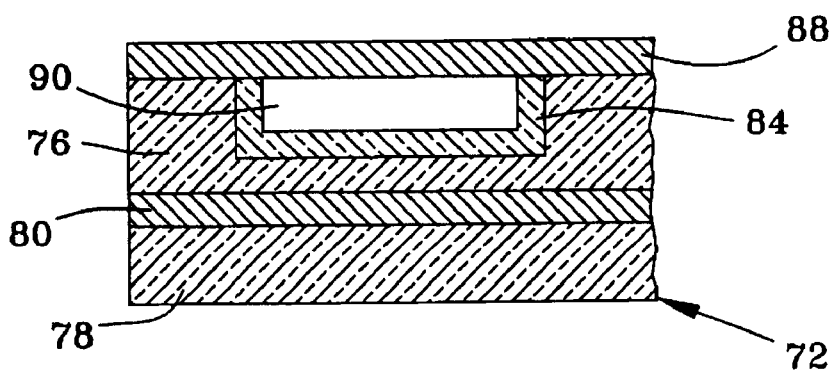

In FIG. 6, the starting material is shown as a silicon-on-insulator (SOI) wafer 72 on which masking layers 74 are grown or deposited. The wafer 72 comprises a P-type silicon layer 76 on a P-type substrate 78, separated by a buried oxide layer 80. As shown in FIG. 7, a trench 82 is etched in the surface of the wafer 72, and the etched surfaces 84 of the trench 82 are heavily doped with boron, germanium or another p-type dopant, such as aluminum, gallium or indium. Doping can be accomplished using solid, gaseous and spindiffusion sources, ion implantation, and through the use of doping an epitaxial layer. The use of germanium as the dopant can avoid higher stresses associated with heavy boron doping. Defects associated with heavy doping can be avoided by polishing the upper wafer surface or masking this surface as shown in FIGS. 6 and 7. If used, the mask is removed before bonding the SOI wafer 72 to a second wafer 86 depicted in FIG. 8 as being processed to have a P+ doped silicon layer 88. In FIG. 9, the wafers 72 and 86 have been bonded together, such as by fusion bonding, with the result that the trench 82 in the SOI wafer 72 now defines an enclosed passage 90 between the wafers 72 and 86, with the walls of the passage 90 defined by doped silicon as a result of the doped etched surfaces 84 of the SOI wafer 72 and the doped silicon layer 88 of the second wafer 86. The undoped portion of the second wafer 86 is then removed in FIG. 10 by an etchant selective to undoped silicon, after which the exposed doped silicon layer 88 is patterned to form a trench (not shown) that will define the exterior of the tube 14.

Figure 11:
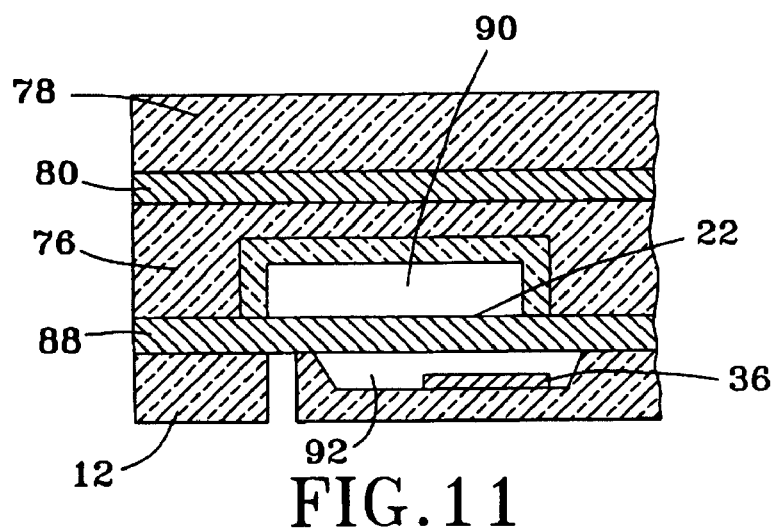
Figure 12:
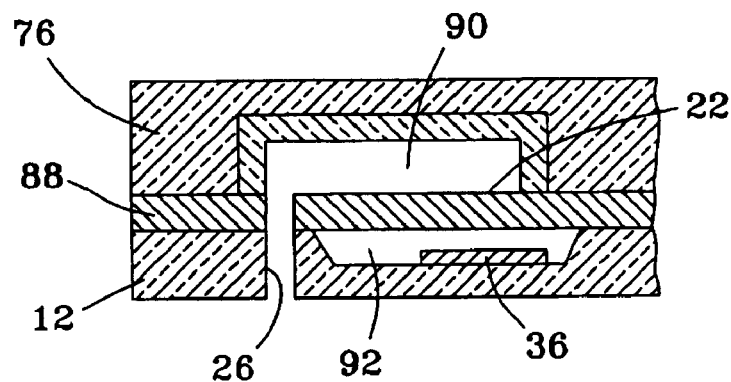

The remaining portions of the doped silicon layer 88 are then bonded to the substrate 12 so that a portion of the doped silicon layer 88 forms the bridge portion 22 of the tube 20 and spans a cavity 92 etched in the surface of the substrate 12 as shown in FIG. 11. This cavity 92 defines the surface 24 of the substrate 12 on which the electrode 36 is formed (FIGS. 2 and 4). In FIG. 12, the P-type substrate 78 and buried oxide layer 80 have been removed by selective etching, thereby releasing the bridge portion 22 of the tube 20 and other suspended structures (e.g., tube 14, cantilevered tube 62) simultaneously fabricated in the surface of the SOI wafer 72. Because the surface of the tube 20 facing the substrate 12 is formed by the doped silicon layer 88, a separate electrode is not required on the tube 20 for driving the bridge portion 22 electrostatically with the electrode 36 on the substrate 12.

The above technique is generally a bulk etching process. Surface thin-film techniques can also be used to form the tubes 14, 20, 52 and 62. An example is to form the tubes 14, 20, 52 and/or 62 of layers deposited on a silicon wafer, bonding the wafer to the substrate 12 so that a portion of the tubes 14, 20, 52 and/or 62 is suspended over a cavity etched in the surface of the substrate 12, and then removing the wafer by selective etching. These and other potential micromachining techniques are within the scope of this invention.

While the invention has been described in terms of certain embodiments, it is apparent that other forms could be adopted by one skilled in the art. Therefore, the scope of the invention is to be limited only by the following claims.

What is claimed is:

1. A sensing device comprising:
   a substrate;
   a first micromachined tube comprising a fluid inlet, a fluid outlet, and a freestanding portion between the fluid inlet and the fluid outlet so as to define a continuous passage for a fluid flowing through the first micromachined tube, the freestanding portion being spaced apart from a first surface of the substrate;
   means for vibrating the freestanding portion of the first micromachined tube at a resonant frequency thereof;
   means for sensing movement of the freestanding portion of the first micromachined tube; and
   at least a second micromachined tube on the substrate, the second micromachined tube being a component of means for sensing a property chosen from the group consisting of motion of the sensing device and pressure, viscosity and temperature of the fluid flowing through the first micromachined tube;

wherein the first and second micromachined tubes comprise portions that are defined by at least one of a bulk etched region of the substrate or an etched film on the substrate.

2. A sensing device according to claim 1, wherein the second micromachined tube is in series with the first micromachined tube such that the fluid flows through both the first and second micromachined tubes.

3. A sensing device according to claim 2, wherein the second micromachined tube has a bridge portion spaced apart from a second surface of the substrate, the bridge portion being operable to deflect toward and away from the second surface in response to a change in pressure of the fluid flowing through the second micromachined tube, the sensing device further comprising means for sensing the proximity of the bridge portion of the second micromachined tube to the second surface of the substrate.

4. A sensing device according to claim 3, further comprising a third micromachined tube on the substrate and in series with the first and second micromachined tubes such that the fluid flows through the second, first and third micromachined tubes, respectively, the third micromachined tube having a bridge portion spaced apart from a third surface of the substrate, the bridge portion of the third micromachined tube being operable to deflect toward and away from the third surface in response to a change in pressure of the fluid flowing through the third micromachined tube.

5. A sensing device according to claim 4, further comprising:
   means for sensing the proximity of the bridge portion of the third micromachined tube to the third surface of the substrate; and
   means for determining the viscosity of the fluid based on pressures sensed with the second and third micromachined tubes.

6. A sensing device according to claim 3, further comprising:
   a stress-sensing member above a third surface of the substrate and through which the fluid does not flow through, the stress-sensing member being configured substantially similarly to the bridge portion of the second micromachined tube, the stress-sensing member being operable to deflect toward and away from the third surface in response to stresses in the substrate;
   means for sensing the proximity of the stress-sensing member to the third surface of the substrate; and
   means for compensating the output of the proximity sensing means of the second micromachined tube with the output of the proximity sensing means of the stress-sensing member.

7. A sensing device according to claim 1, wherein the second micromachined tube thermally communicates with the first micromachined tube for sensing the temperature of the fluid flowing through the first micromachined tube.

8. A sensing device according to claim 7, wherein the second micromachined tube has a cantilevered portion above a second surface of the substrate, the sensing device further comprising:
   means for vibrating the cantilevered portion of the third micromachined tube at a resonant frequency thereof; and
   means for sensing changes in the resonant frequency of the cantilevered portion in response to a change in temperature of the fluid flowing through the first micromachined tube.

9. A sensing device according to claim 8, further comprising a cap hermetically bonded to the substrate so as to define a hermetically-sealed evacuated enclosure containing the second micromachined tube and the freestanding portion of the first micromachined tube.

10. A sensing device according to claim 9, wherein the cap is operable to shield the second micromachined tube from thermal radiation.

11. A sensing device according to claim 9, wherein the cap is operable to selectively transmit thermal radiation to the second micromachined tube for sensing of the thermal radiation.

12. A sensing device according to claim 7, further comprising electrodes contacting portions of the first micromachined tube at the fluid inlet and the fluid outlet thereof, and means for flowing a current between the electrodes and through the first micromachined tube so as to heat the fluid flowing therethrough.

13. A sensing device according to claim 1, further comprising a metal layer on at least one of the first and second micromachined tubes and means for determining the temperature of the fluid flowing therethrough by sensing changes in electrical resistance of the metal layer.

14. A sensing device according to claim 1, further comprising at least two metal layers in contact with the fluid flowing within the sensing device, the at least two metal layers being coupled to means for sensing a property chosen from the group consisting of electrical conductivity, dielectric constant and pH of the fluid.

15. A sensing device according to claim 1, wherein the second micromachined tube comprises a suspended member operable to deflect toward and away from a second surface of the substrate in response to motion of the sensing device, the sensing device further comprising means for sensing the proximity of the suspended member to the second surface of the substrate.

16. A sensing device according to claim 1, further comprising a stress-sensing member above a third surface of the substrate and through which the fluid does not flow through, the stress-sensing member being operable to deflect toward and away from the third surface in response to stresses in the substrate, the sensing device further comprising means for sensing the proximity of the stress-sensing member to the third surface of the substrate.

17. A sensing device according to claim 16, wherein the stress-sensing member is configured and freestanding substantially similarly to the freestanding portion of the first micromachined tube, the sensing device further comprising means for compensating the output of the movement sensing means of the first micromachined tube with the output of the proximity sensing means of the stress-sensing member.

18. A sensing device according to claim 1, wherein the first micromachined tube is operable to sense a property chosen from the group consisting of density and mass flow rate of the fluid flowing through the first micromachined tube.

19. A sensing device according to claim 18, further comprising electrodes contacting portions of the first micromachined tube at the fluid inlet and the fluid outlet thereof, and means for flowing a current between the electrodes and through the first micromachined tube so as to heat the fluid flowing therethrough.

20. A sensing device according to claim 1, wherein the second micromachined tube is in series with the first micromachined tube such that the fluid flows through both the first and second micromachined tubes, the second micromachined tube having walls contacted by the fluid as the fluid flows therethrough, the walls of the second micromachined tube being heavily doped p-type.

21. A sensing device comprising:

a semiconductor substrate;

a first tube comprising a fluid inlet, a fluid outlet, and a freestanding portion between the fluid inlet and the fluid outlet so as to define a continuous passage for a fluid flowing through the first tube, the freestanding portion being spaced apart from a first surface of the substrate and comprising a micromachined portion of the substrate;

means for vibrating the freestanding portion of the first tube at a resonant frequency thereof;

means for sensing movement of the freestanding portion of the first tube and thereby sense a property chosen from the group consisting of density and mass flow rate of the fluid flowing through the first tube; and at least a second tube comprising a micromachined portion of the substrate, the second tube being in series with the first tube such that the fluid flows through both the first and second tubes, the second tube being a component of means for sensing a property chosen from the group consisting of pressure, viscosity and temperature of the fluid flowing through the first tube.

22. A sensing device according to claim 21, wherein the second tube has a bridge portion spaced apart from a second surface of the substrate, the bridge portion having a width wider than a width of the freestanding portion of the first tube and being operable to deflect toward and away from the second surface in response to a change in pressure of the fluid flowing through the second tube, the sensing device further comprising means for sensing the proximity of the bridge portion of the second tube to the second surface of the substrate.

23. A sensing device according to claim 22, further comprising:

a third tube on the substrate and in series with the first and second tubes such that the fluid flows through the second, first and third tubes, respectively, the third tube having a bridge portion spaced apart from a third surface of the substrate, the bridge portion of the third tube having a width approximately equal to the width of the bridge portion of the second tube and being operable to deflect toward and away from the third surface in response to a change in pressure of the fluid flowing through the third tube;

means for sensing the proximity of the bridge portion of the third tube to the third surface of the substrate; and means for determining the viscosity of the fluid based on pressures sensed with the second and third tubes.

24. A sensing device according to claim 21, further comprising:

a stress-sensing member above a third surface of the substrate and through which the fluid does not flow through, the stress-sensing member being configured substantially similarly to the bridge portion of the second tube, the stress-sensing member being operable to deflect toward and away from the third surface in response to stresses in the substrate;

means for sensing the proximity of the stress-sensing member to the third surface of the substrate; and means for compensating the output of the proximity sensing means of the second tube with the output of the proximity sensing means of the stress-sensing member.

25. A sensing device according to claim 21, further comprising a third tube having a cantilevered portion above a third surface of the substrate and that thermally communicates with the first tube for sensing the temperature of the fluid flowing through the first tube, the sensing device further comprising:

means for vibrating the cantilevered portion of the third tube at a resonant frequency thereof; and means for sensing changes in the resonant frequency of the cantilevered portion in response to a change in temperature of the fluid flowing through the first tube.

26. A sensing device according to claim 25, further comprising a cap hermetically bonded to the substrate so as to define a hermetically-sealed evacuated enclosure containing the third tube and the freestanding portion of the first tube, the cap being operable to shield the third tube from thermal radiation.

27. A sensing device according to claim 25, further comprising electrodes contacting portions of the first tube at the fluid inlet and the fluid outlet thereof, and means for flowing a current between the electrodes and through the first tube so as to heat the fluid flowing therethrough.

28. A sensing device according to claim 21, further comprising a metal layer on at least one of the first and second tubes and means for determining the temperature of the fluid flowing therethrough by sensing changes in electrical resistance of the metal layer.

29. A sensing device according to claim 21, further comprising at least two metal layers in contact with the fluid flowing within the sensing device, the at least two metal layers being coupled to means for sensing a property chosen from the group consisting of electrical conductivity, dielectric constant and pH of the fluid.

30. A sensing device according to claim 21, further comprising a cantilevered member above a third surface of the substrate, the cantilevered member being operable to deflect toward and away from the third surface in response to motion of the sensing device, the sensing device further comprising means for sensing the proximity of the cantilevered member to the third surface of the substrate.

31. A sensing device according to claim 21, further comprising:

a stress-sensing member above a third surface of the substrate and through which the fluid does not flow through, the stress-sensing member is configured and freestanding substantially similarly to the freestanding portion of the first tube, the stress-sensing member being operable to deflect toward and away from the third surface in response to stresses in the substrate;

means for sensing the proximity of the stress-sensing member to the third surface of the substrate; and means for compensating the output of the movement sensing means of the first tube with the output of the proximity sensing means of the stress-sensing member.

32. A sensing device according to claim 21, wherein the second tube has walls contacted by the fluid as the fluid flows therethrough, the walls of the second tube being heavily doped p-type.

* * * * *